(12) United States Patent
Ullrich

(10) Patent No.: US 6,358,943 B1
(45) Date of Patent: Mar. 19, 2002

(54) N-SUBSTITUTED INDOLINES AS ESTROGENIC AGENTS

(75) Inventor: John W. Ullrich, Schwenksville, PA (US)

(73) Assignee: American Home Products Corporation, Madison, NJ (US)

( * ) Notice: Subject to any disclaimer, the term of this patent is extended or adjusted under 35 U.S.C. 154(b) by 0 days.

(21) Appl. No.: 09/513,112

(22) Filed: Feb. 25, 2000

Related U.S. Application Data

(60) Provisional application No. 60/160,064, filed on Mar. 4, 1999.

(51) Int. Cl.⁷ .................. A61K 31/55; A61K 31/535; A61K 31/445; A61K 31/40; A61K 31/405
(52) U.S. Cl. .................. 514/217.08; 514/235.2; 514/323; 514/414; 514/415; 540/602; 544/144; 546/201; 548/465; 548/506
(58) Field of Search .................. 514/217.08, 235.2, 514/323, 414, 415; 540/602; 544/144; 546/201; 548/465, 506

(56) References Cited

U.S. PATENT DOCUMENTS

| | | | |
|---|---|---|---|
| 4,943,572 A | 7/1990 | Von Angerer | 514/235.2 |
| 5,686,481 A | 11/1997 | Elliott et al. | 514/414 |

FOREIGN PATENT DOCUMENTS

| | | |
|---|---|---|
| EP | 0802183 | 10/1997 |
| WO | 9603375 | 2/1996 |

OTHER PUBLICATIONS

Von Angerer, Chem. Abs., 1983, 99(7), 53886u.
Von Angerer et al., J. Med. Chem., 1987, 30, 131–136.
Von Angerer et al., J. Med. Chem., 1990, 33, 2635–2640.

*Primary Examiner*—Brenda Coleman
(74) *Attorney, Agent, or Firm*—Arnold S. Milowsky

(57) ABSTRACT

This invention provides compounds of the formula

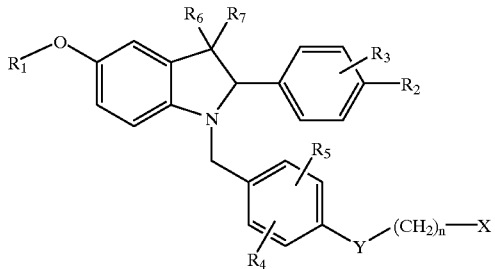

wherein $R_1$, $R_2$, $R_3$, $R_4$, $R_5$, $R_6$, $R_7$, X, n and Y, are as defined in the specification, or a pharmaceutically acceptable salt thereof, as well as pharmaceutical compositions and methods utilizing the compounds for treating or preventing disease states or syndromes which are caused or associated with an estrogen deficiency or an excess of estrogen utilizing these compounds.

15 Claims, No Drawings

N-SUBSTITUTED INDOLINES AS ESTROGENIC AGENTS

This application claims the benefit of U.S. Provisional Application No. 60/160,064, filed Mar. 4, 1999.

The present invention relates to new N-substituted indoline compounds which are useful as estrogenic agents, as well as pharmaceutical compositions and methods of treatment utilizing these compounds.

BACKGROUND OF THE INVENTION

Estrogen replacement therapy has been well established as the treatment of choice in women for the prevention of osteoporosis. [C. Christiansen, R. Lindsay, Estrogen, Bone Loss and Preservation, Osteoporosis International, 1, 15–21 (1990)] The problem with unopposed estrogen therapy is that proliferative effects on the uterus may occur and be associated with endometriosis and/or endometrial cancer. Although less clear, unopposed estrogen replacement therapy has been implicated in increasing the incidence of breast tumor formation. Non-steroidal antiestrogen drugs such as Tamoxifen have been used in the treatment of breast cancer. Tamoxifen has been shown to exert an estrogen-like effect on bone in humans while acting as an antagonist in uterine tissue. However, demonstration of partial agonistic effects in the uterus is of some concern. A recent antiestrogen drug, Raloxifene, Lilly's benzothiophene, is a non-steroidal antiestrogen which appears to be more tissue selective. While possessing the ability to spare bone, it has been demonstrated to stimulate uterine growth in animal models to a lesser degree than Tamoxifen. A review on the tissue selective action of estrogen receptor modulators has recently appeared. [T. A. Grese and J. A. Dodge In "Ann. Rep. in Med. Chem." J. A. Bristol, Ed. Academic Press, New York, 1996, p.181]

The use of indoles as estrogen antagonists has been reported by Von Angerer, Chemical Abstracts, Vol. 99, No. 7 (1983), Abstract No. 53886u. Also, see, J. Med. Chem. 1990, 33, 2635–2640; J. Med. Chem. 1987, 30, 131–136. Also see Ger. Offen., DE 3821148 A1 891228 and WO 96/03375.

The compounds described in the present invention possess moderate binding to the estrogen receptor (ER) and have potential use in treating osteoporosis, prostatic hypertrophy, breast cancer and endometrial cancer.

DESCRIPTION OF THE INVENTION

N-substituted indolines of this invention are tissue-selective estrogen agonists/antagonists useful for the treatment of diseases associated with estrogen deficiency. They include compounds of the formula:

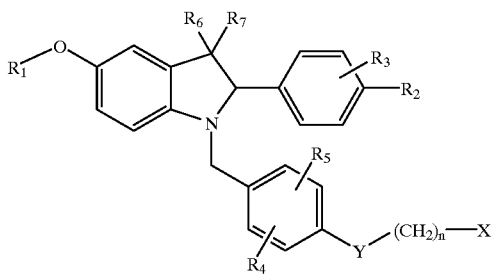

wherein:

$R_1$ is H or benzyl;
$R_2$ is H, —OH, or —O—benzyl;
$R_3$, $R_4$, and $R_5$ are independently selected from H, cyano, $C_1$–$C_6$ alkyl (straight chain or branched), trifluoromethyl, —OH or the $C_1$–$C_{12}$ esters (straight chain or branched) or $C_1$–$C_{12}$ alkyl ethers (straight chain or branched or cyclic) thereof, halogens, or $C_1$–$C_6$ halogenated ethers, preferably $C_1$–$C_3$ halogenated ethers, including trifluoromethyl ether and trichloromethyl ether;
$R_6$ is H or $C_1$–$C_6$ alkyl;
$R_7$ is $C_1$–$C_6$ alkyl;
n is 2 to 3;
Y is O or S; and
X is

R' is selected from $C_1$–$C_6$ lower alkyl or the moieties:

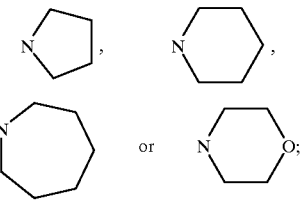

or a pharmaceutically acceptable salt thereof.

Among the more preferred compounds of this invention are those in which Y is O, n is 2 and $R_3$, $R_4$, and $R_5$ are independently selected from H, OH or halogen. It will be understood that the number of carbons in the alkyl groups of moieties $R_6$ and $R_7$ may be selected independently of each other.

The invention includes acceptable salt forms formed from the addition reaction with either inorganic or organic acids. Inorganic acids such as hydrochloric acid, hydrobromic acid, hydroiodic acid, sulfuric acid, phosphoric acid, nitric acid as well as organic acids such as acetic acid, propionic acid, citric acid, maleic acid, malic acid, tartaric acid, phthalic acid, succinic acid, methanesulfonic acid, toluenesulfonic acid, napthalenesulfonic acid, camphorsulfonic acid, benzenesulfonic acid are useful. It is known that compounds possessing a basic nitrogen can be complexed with many different acids (both protic and not protic) and usually it is preferred to administer a compound of this invention in the form of an acid addition salt. Additionally, this invention includes quaternary ammonium salts of the compounds herein, which can be prepared by reacting the nucleophilic amines of the side chain with a suitably reactive alkylating agent such as an alkyl halide or benzyl halide.

The compounds of the invention are partial estrogen agonists and display high affinity for the estrogen receptor. Unlike many estrogens, however, many of these compounds do not cause increases in uterine wet weight. These compounds are antiestrogenic in the uterus and can completely antagonize the trophic effects of estrogen agonists in uterine tissue. Due to the tissue selective nature of these compounds, they are useful in treating or preventing in a mammal disease states or syndromes which are caused or associated with an estrogen deficiency or an excess of estrogen.

The present compounds have the ability to behave like estrogen agonists by lowering cholesterol and preventing bone loss. These compounds are useful for treating many maladies which result from estrogen excess or deficiency including osteoporosis, prostatic hypertrophy, male pattern baldness, ovarian cancer, infertility, breast cancer, endometrial cancer, cardiovascular disease, contraception, Alzheimer's disease, cognitive decline and other CNS disorders, as well as certain cancers, including melanoma, prostrate cancer, cancers of the colon, CNS cancers, among others. Additionally, these compounds can be used for hormone replacement therapy in post-menopausal women or in other estrogen deficiency states where estrogen supplementation would be beneficial.

The compounds of this invention may also be used in methods of treatment for bone loss, which may result from an imbalance in an individuals formation of new bone tissues and the resorption of older tissues, leading to a net loss of bone. Such bone depletion results in a range of individuals, particularly in post-menopausal women, women who have undergone hysterectomy, those receiving or who have received extended corticosteroid therapies, those experiencing gonadal dysgenesis, and those suffering from Cushing's syndrome. Special needs for bone replacement can also be addressed using these compounds in individuals with bone fractures, defective bone structures, and those receiving bone-related surgeries and/or the implantation of prosthesis. In addition to those problems described above, these compounds can be used in treatments for osteoarthritis, hypocalcemia, hypercalcemia, Paget's disease, osteomalacia, osteohalisteresis, multiple myeloma and other forms of cancer having deleterious effects on bone tissues. Methods of treating the maladies listed herein are understood to comprise administering to an individual in need of such treatment a pharmaceutically effective amount of one or more of the compounds of this invention or a pharmaceutically acceptable salt thereof. This invention also includes pharmaceutical compositions utilizing one or more of the present compounds, and/or the pharmaceutically acceptable salts thereof, along with one or more pharmaceutically acceptable carriers, excipients, etc.

It is understood that the dosage, regimen and mode of administration of these compounds will vary according to the malady and the individual being treated and will be subject to the judgement of the medical practitioner involved. It is preferred that the administration of one or more of the compounds herein begin at a low dose and be increased until the desired effects are achieved.

Effective administration of these compounds may be given at an effective dose of from about 0.1 mg/day to about 1,000 mg/day. Preferably, administration will be from about 10 mg/day to about 600 mg/day in a single dose or in two or more divided doses. Such doses may be administered in any manner useful in directing the active compounds herein to the recipient's bloodstream, including orally, parenterally (including intravenous, intraperitoneal and subcutaneous injections), and transdermally. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, , xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Oral formulations herein may utilize standard delay or time release formulations to alter the absorption of the active compound(s). Suppository formulations may be made from traditional materials, including cocoa butter, with or without the addition of waxes to alter the suppository's melting point, and glycerin. Water soluble suppository bases, such as polyethylene glycols of various molecular weights, may also be used.

Compounds of this invention may be prepared by methods known in the art. For instance, the starting or core indoline can be prepared by the general methods of Schemes 1 and 2, below.

Scheme 1

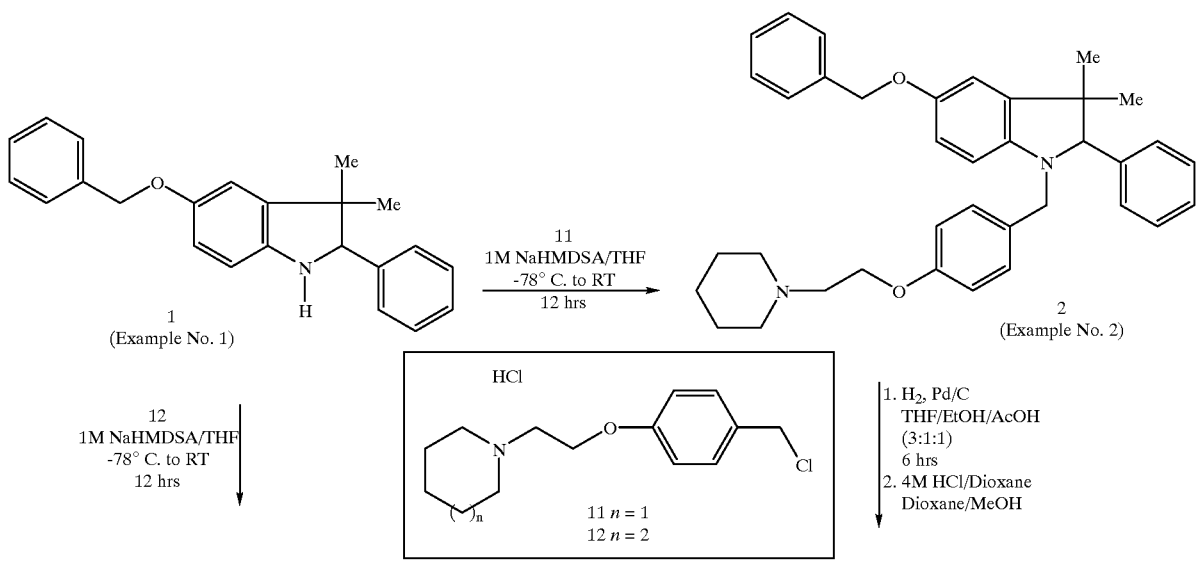

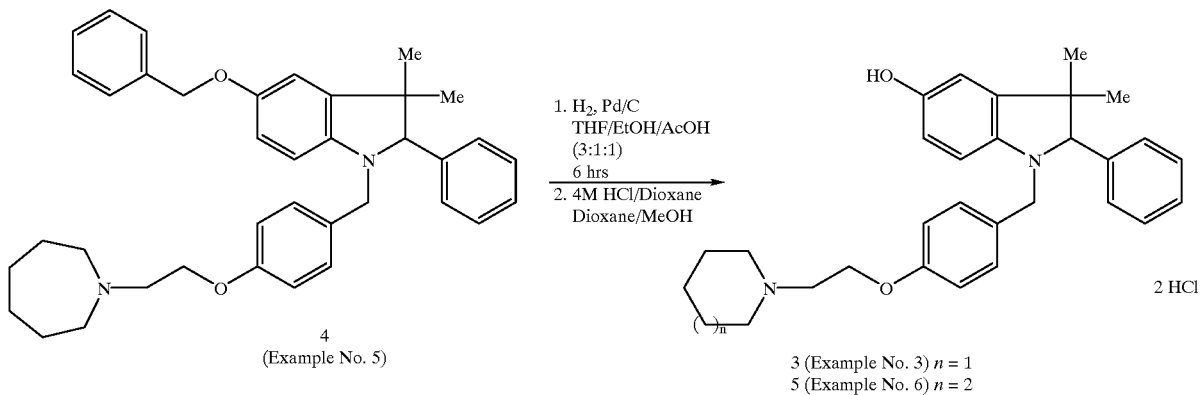
Scheme 2
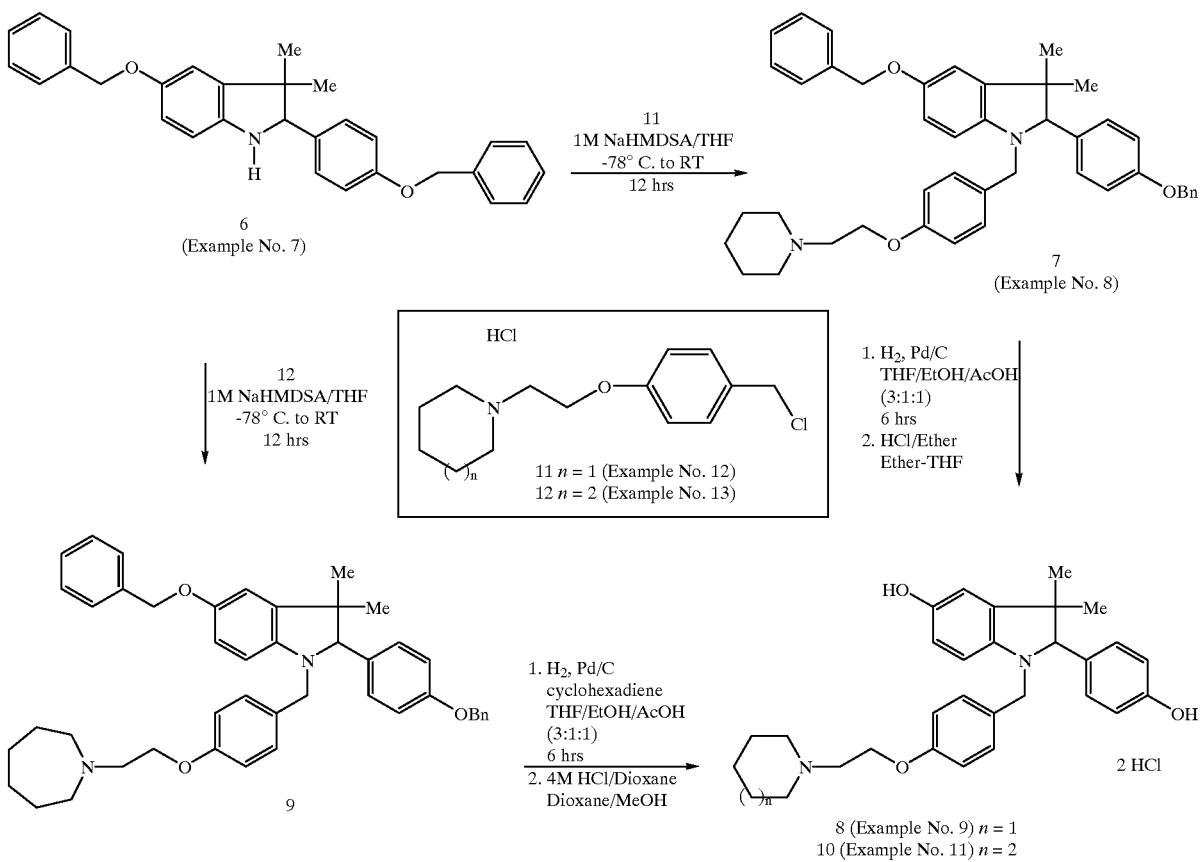
The synthesis of the compounds in this invention may be accomplished by deprotonation then alkylation of the core template 1 or 6 using the sodium salt of hexamethyldisilyl amide and the desired side chain. (Schemes 1 and 2)
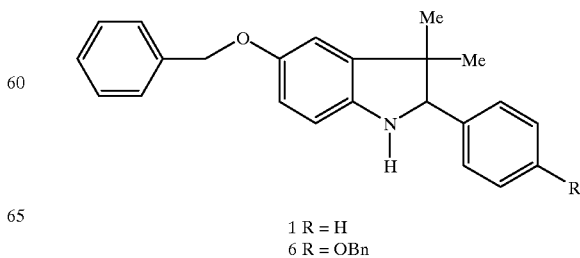

EXAMPLE NO. 1

(Compound No. 1 in Scheme 1)

5-Benzyloxy-3,3-dimethyl-2-phenyl-2,3-dihydro-1H-indole

The protected dihydro-indoles 1 and 6, shown above, were used as the core template to synthesize compounds 3 (Example No. 3), 5 (Example No. 6), 8 (Example No. 9) and 10 (Example No. 11). These material templates were prepared using the general method described by Letcher, R. M. et. al., J. Chem. Soc. Perkin Trans., 1993, Vol. 1, pp. 939–944. For example, Template 1 was prepared from 4-benzyloxyphenyl hydrazine and isobutyrophenone.

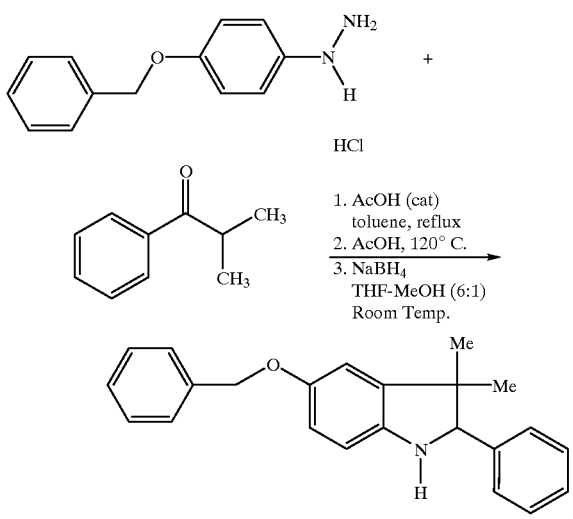

To a solution of 4-benzyloxy-phenyl hydrazine HCl (2.5 g, 11.7 mmol) and isobutyrophenone (2.1 g, 14.0 mmol) in 20 ml toluene was added acetic acid (cat) and the resulting solution was refluxed with azeotropic removal of $H_2O$ for 14 hours. The reaction mixture was cooled to room temperature and concentrated. The resulting semi-solid was taken up in acetic acid and refluxed for 12 hours. The reaction mixture was cooled to room temperature and concentrated. The semi-solid residue was taken up in ether and neutralized with $K_2CO_3$. The ether layer was dried and concentrated. The resulting solid imine was dissolved in THF-MeOH (6:1), cooled to 0° C. and $NaBH_4$ (0.53 g, 13.2 mmol) was added. The solution was allowed to warm to room temperature and stirred for 0.5 hours. The reaction mixture was poured into 15% HCl and made basic with $K_2CO_3$. The organic layer was separated, washed with brine, dried over $NaSO_4$, and concentrated. The crude product was purified by column chromatography ($SiO_2$, hexane-ethyl acetate (9:1). The desired template, 1, was isolated as an orange semi-solid (2.9 g, 75%): $^1$H NMR (CDCl$_3$) δ d 0.7 (s, 3H), 1.4 (s, 3H), 3.85 (br.s. 1H), 4.8 (s. 1H), 5.0 (s, 2H), 6.62 (d, 1H), 6.67 (s, 1H), 6.8 (dd, 1H), 7.3–7.5 (m, 10H); $^{13}$C-NMR (CDCl$_3$) δ 24.3 (q), 26.3 (q), 45.5 (s), 71.0 (t), 74.9 (d), 110.4 (d), 110.9 (d), 113.0 (d), 127.4, 127.5 127.6, 127.8, 128, 128.5 (d), 137.6 (s), 139.7 (s), 139.9 (s), 143.4 (s), 152.9 (s); IR (film) 3390, 3040, 2980, 1490, 1050 cm$^{-1}$; mass spectrum m/e 330 (M+1); CHN calc. for $C_{23}H_{23}NO$

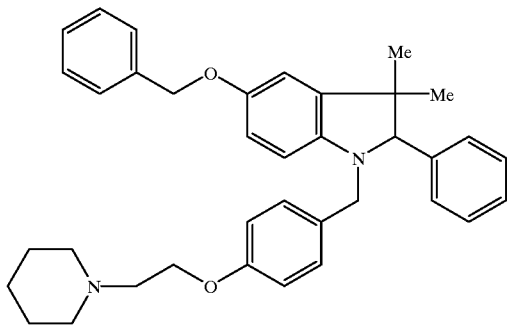

EXAMPLE NO. 2

(Compound No. 2 in Scheme 1)

5-Benzyloxy-3,3-dimethyl-2-phenyl-1-[4-(2-piperidin-1-yl-ethoxy)-benzyl]-2,3-dihydro-1H-indole To a solution of 5-benzyloxy-indoline 1 (0.2 g, 0.61 mmol) and piperidine ethoxy benzylbromide 11 (0.18 g, 0.61 mmol) in 3 mL THF at −78° C. was added 1.53 mL, (1.53 mmol, 1M, NaHMDSA-THF, 2.5 eq.). The reaction mixture was allowed to warm to room temperature and stirred for 12 hrs. The reaction was then poured into water, extracted with EtOAc. The organic layer was dried with $MgSO_4$ and concentrated. The product was purified by flash chromatography (15% EtOAc-Hexane) to give the desired N-alkylated indoline 2 as a yellow foam.

$^1$H-NMR (CDCl$_3$) δ 0.79 (s, 3H), 1.34 (s, 3H), 1.4 (m, 2H), 1.6 (m, 4H), 2.5 (m, 4H), 2.8 (t, 2H), 3.82 (d, AB q, 1H), 4.1 (t, 2H), 4.2 (s, 1H), 4.25 (d, AB q, 1H), 5.0 (s, 1H), 6.33 (d, 1H), 6.6 (dd, 1H), 6.7 (dd, 1H), 6.8 (d, 2H), 7.2 (d, 2H), 7.3–7.45 (m, 10H); $^{13}$C-NMR (CDCl$_3$) δ 24.18(t), 25.05 (q), 25.9 (t), 26.0 (q), 44.5 (s), 51.5, 55.0, 57.9, 65.9, 70.9 (t), 80.5 (d), 109.0, 110.7, 112.5, 114.4, 127.53, 127.55, 127.7, 128.1, 128.5, 128.6 (d), 130.6, 137.6, 137.7, 140.4, 145.3, 152.6, 157.72 (s); mass spectrum m/e 547 (M+1).

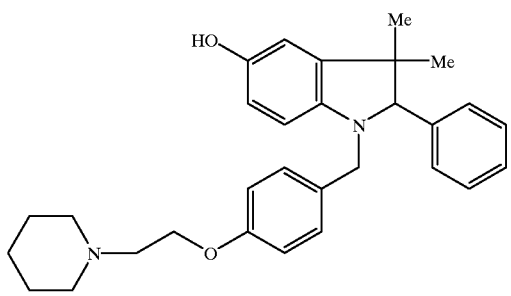

EXAMPLE NO. 3

(Compound No. 3 in Scheme 1)

3,3-Dimethyl-2-phenyl-1-[4-(2-piperidin-1-yl-ethoxy)-benzyl]-2.3-dihydro-1H-indol-5-ol To a solution of the N-alkylated indoline 2 (0.14 g, 0.26 mmol) in 8 mL (THF-EtOH-AcOH, 5:2:1) was added 0.14 g (10% Pd/C) followed by 0.25 mL cyclohexadiene (10 eq.) The reaction mixture was stirred at RT. for 7 hrs. The reaction mixture was filtered through celite, concentrated. The residue was taken up in EtOAc, washed with NaHCO$_3$. The organic layer was dried with MgSO$_4$ and concentrated. The product was purified by flash chromatography (8% MeOH-Methylene chloride) to give the desired phenol-indoline 3.

$^1$H-NMR (CDCl$_3$) δ 0.65 (s, 3H), 1.25 (s, 3H), 1.3–1.5 (m, 6H), 2.4 (m, 6H), 2.65 (m, 2H), 3.7 (d, AB q, 1H), 4.1 (m, 1H), 4.25 (d, AB q, 1H), 6.28 (d, 1H), 6.4 (dd, 1H), 6.5(S, 1H), 6.8(d, 2H), 7.1(d, 2H), 7.3–7.45 (m, 5H), 8.6 (S, 1H); mass spectrum m/e 457 (M+1).

EXAMPLE NO. 4

(Compound No. 3 (HCl Salt) in Scheme 1)

3,3-Dimethyl-2-phenyl-1-[4-(2-piperidin-1-yl-ethoxy)-benzyl-]-2,3-dihydro-1H-indol-5-ol (HCl)

A solution of the phenol indoline 3 (0.043 g, 0.11 mmol) in 2 mL of Et$_2$O-THF (4-1) is treated with 1.2 eq (1M HCl/Et$_2$O). The reaction mixture is then stirred for 2 hours, concentrated giving the desired HCl salt.

EXAMPLE NO. 5

(Compound No. 4 in Scheme 1)

1-[4-(2-Azepan-1-yl-ethoxy)-benzyl]-5-benzyloxy-3,3-dimethyl-2-phenyl-2,3-dihydro-1H-indole Prepared as described above for compound 2.

$^1$H-NMR (CDCl$_3$) δ 0.8 (s.3H), 1.35 (s. 3H), 1.65 (m, 8H), 2.8 (m, 9H), 3.0 (t. 2H), 3.8 (A–B q, 1H), 4.1 (t. 2H), 4.2 (s, 1H), 4.3 (AB q, 1H), 4.95 (s, 2H), 6.35 (d, 1H), 6.65 (dd, 1H), 7.5 (s, 1H), 6.85 (d. 2H), 7.2 (d, 2H), 7.25–7.5 (m, 10H); mass spectrum m/e 561 (M+1).

EXAMPLE NO. 6

(Compound No. 5 in Scheme 1)

1-[4-(2-Azepan-1-yl-ethoxy)-benzyl]-3,3-dimethyl-2-phenyl-2,3-dihydro-1H-indol-5-ol Prepared as described above for compound 3.

$^1$H-NMR (DMSO-d$_6$) δ 0.6 (5, 3H), 1.15 (S, 3H), 1.4 (m, 8H), 2.6 (m, 4H), 2.7 (m, 2H), 3.55 (ABq, 1H), 3.8 (7, 2H), 3.9 (S, 1H), 4.05 (ABq, 1H), 6.15 (d, 1H), 6.25 (d, 1H), 6.35 (S, 1H), 6.7 (D, 2H), 7.0 (d, 2H), 7.2–7.4 (m, 5H), 8.5 (S, 1H); mass spectrum m/e 471 (M+1).

EXAMPLE NO. 7

(Compound No. 6 in Scheme 2)

5-Benzyloxy-2-(4-benzyloxy-phenyl)-3,3-dimethyl-2,3-dihydro-1H-indole

The title compound was prepared using the general method described by Letcher, R. M. et. al., J. Chem. Soc. Perkin Trans., 1993, Vol. 1, pp. 939–944. (See Example No. 1, above) from 4-benzyloxyphenyl hydrazine and (4-benzyloxy)-phenyl isopropyl ketone.

$^1$H-NMR (CDCl$_3$) δ 0.7 (s, 3H), 1.35 (s, 3H), 3.85 (br. s, 1H), 4.5 (S, 1H), 5.0 (s, 2H, 5.1 (s, 2H), 6.6 (d, 1H), 6.7 (s, 1H), 6.75 (s, 1H), 6.95 (d, 2H), 7.25–7.5 (m, 12H). $^{13}$C-NMR (CDCl$_3$) d 24.2, 26.2 (q), 45.5 (s), 70.0, 71.0 (t), 74.5 (d), 109.4, 110.9, 112.9, 114.3, 127.5, 127.6, 127.8, 127.9, 128.5, 128.6, (d), 132.2, 137.04, 137.6, 139.8, 143.4, 152.9, 158.3 (s); mass spectrum m/e 436 (M+1).

EXAMPLE NO. 8

(Compound No. 7 in Scheme 2)

5-Benzyloxy-2-(4-benzyloxy-phenyl)-3,3-dimethyl-1-[4-(2-piperidin-1-yl-ethoxy)-benzyl]2,3-dihydro-1H-indole Prepared as described above for compound 2.

$^1$H-NMR (CDCl$_3$) δ 0.75 (s, 3H), 1.2 (s, 3H), 1.6–1.8 (m, 6H), 2.75 (t.2H), 3.2–3.85 (m, 4H), 4.05 (t.2H), 4.7 (br.s, 1H), 4.35 (br. s 2H), 5.0 (s, 2H), 5.1 (s, 2H), 6.3 (d. 2H), 6.5 (m, 2H), 6.6 (d, 2H), 6.85 (d. 2H), 6.95 (d, 2H), 7.05 (d, 2H), 7.2–7.5 (m, 8H), 7.5 (br. s. 1H).

EXAMPLE NO. 9

(Compound No. 8 in Scheme 2)

2-(4-Hydroxy-phenyl)-3,3-dimethyl-1-[4-(2-piperidin-1-yl-ethoxy)-benzyl]-2,3-dihydro-1H-indol-5-ol Prepared as described above for compound 3.

$^1$H-NMR (DMSO) δ 0.75 (s, 3H), 1.2 (s, 3H), 1.6–1.8 (m, 6H), 2.75 (t.2H), 3.2–3.85 (m, 4H), 4.05 (t.2H), 4.7 (br.s, 1H), 4.35 (br. s 2H), 6.3 (d. 2H), 6.5 (m, 2H), 6.6 (d, 2H), 6.85 (d. 2H), 7.05 (d, 2H), 7.5 (br. s. 1H); mass spectrum m/e 473 (M+1).

EXAMPLE NO. 10

(Compound No. 9 in Scheme 2)

5-Benzyloxy-2-(4-benzyloxy-phenyl)-3,3-dimethyl-1-[4-(2-Azepan-1-yl-ethoxy)-benzyl]-2,3-dihydro-1H-indole Prepared as described above for compound 2.

$^1$H-NMR (CDCl$_3$) δ 0.8 (s, 3H), 1.35 (s, 3H), 1.6–1.8 (m, 6H), 2.8 (br.s, 4H) 3.1 (t, 2H), 3.8 (AB q, 1H), 4.1 (t. 3H), 4.25 (AB q. 1H), 4.95 (s, 2H), 5.1 (s, 2H), 6.3 (d, 1H), 6.6 (d, 1M), 6.75 (s, 1H), 6.8 (d, 2H), 6.95 (m, 3H), 7.1 (d, 1H), 7.2 (d, 2H), 7.3 (m, 8H), 7.55 (d, 1H), 8.1 (d, 1H).

EXAMPLE NO. 11

Compound No. 10 in Scheme 2):

1-[4-(2-Azepan-1-yl-ethoxy)-benzyl]-2-(4-hydroxy-phenyl)-3,3-dimethyl-2,3-dihydro-1H-indol-5-ol Prepared as described above for compound 3.

$^1$H-NMR (CDCl$_3$) δ 0.8 (s, 3H), 1.15 (s, 3H), 1.6 (t, 2H), 1.7 (m, 4H), 3.1 (m,2H), 3.3–3.5 (m, 4H), 4.2 (t, 2H), 4.3–4.5 (m 2H), 6.7 (d, 4H), 6.8 (d, 4H) 6.9 (d, 2H) 2.1 (d, 2H), 7.3 (br. S, 1H).

EXAMPLE NO. 12

Compound No. 11 in Scheme 2)

1-[2-(4-Chloromethyl-phenoxy)-ethyl]-piperidine

This material is prepared from the amino alcohol 1-[2-(4-Hydroxymethyl-phenoxy)-ethyl]piperidine by treatment with thionyl chloride in THF at 0° C. Resulting solid is used without further purification.

$^1$H-NMR (CDCl$_3$) δ 1.7–1.9 (m, 6H), 2.5 (br. s, 4H), 2.7 (t, 2H), 4.1 (t, 2H), 4.6 (s, 2H), 6.9 (d, 2H), 7.3 (d, 2H). 12.1 (br s, 1H).

EXAMPLE NO. 13

(Compound No. 12 in Scheme 2)

1-[2-(4-Chloromethyl-phenoxy)-ethyl]-azepane

This material is prepared from the amino alcohol 1-[2-(4-Hydroxymethyl-phenoxy)-ethyl]azapine by treatment with thionyl chloride in THF at 0° C. Resulting solid is used without further purification.

$^1$H-NMR (CDCl$_3$) δ 1.7 (m, 2H), 1.9 (m, 4H), 2.2 (m, 2H), 3.1 (m, 2H), 3.4 (7, 2H), 3.6 (t.2H), 6.9 (d, 2H), 7.3 (d, 2H), 12.5 (1H).

Receptor Binding Assay

Objective:

To identify compounds that compete with 17β-estradiol for estrogen receptor (ER) binding. The widely accepted mode for estrogenic action is via its high affinity receptor protein. Compounds which demonstrate an ability to bind to the ER may then regulate physiological processes associated with estrogen action.

Procedure:

Receptor Preparation: CHO cells overexpressing the estrogen receptor are grown in 150 mm$^2$ dishes in DMEM+ 10% dextran coated charcoal, stripped fetal bovine serum. The plates are washed twice with PBS and once with 10 mM Tris-HCl, pH 7.4, 1 mM EDTA. Cells are harvested by scraping the surface and then the cell suspension is placed on ice. Cells are disrupted with a hand-held motorized tissue grinder using two, 10-second bursts. The crude preparation is centrifuged at 12,000×g for 20 min. followed by a 60 min spin at 100,000×g to produce a ribosome-free cytosol. The cytosol is frozen and stored at −80° C. Protein concentration of the cytosol is estimated using the BCA assay with BSA as the reference standard protein.

Binding Assay conditions:

The competition assay is performed in a 96-well plate (polystyrene*) which binds <2.0% of the total input [3H]-17β-estradiol. Each data point is gathered in triplicate. 100 ug/100 ul of the receptor preparation is aliquoted per well. A saturating dose of 2.5 nM [3H]17β-estradiol+competitor (or buffer) in a 50 μl volume is added in the preliminary competition when 100×and 500×competitor concentrations are evaluated. For an IC$_{50}$ determination, where 12 concentrations of competitor are evaluated, only 0.8 nM [3H]17β-estradiol is used. The plate is incubated at room temperature for 2.5 h. At the end of this incubation period 150 μl of ice-cold dextran coated charcoal (5% activated charcoal coated with 0.05% 69K dextran) is added/well and the plate is immediately centrifuged at 900×g for 5 minutes at 4° C. 200 μl of the supernatant solution is removed for scintillation counting. Samples are counted to 2% or 10 min, whichever occurs first.

*Because polystyrene absorbs a small amount of [3H] 17β-estradiol, wells containing radioactivity and cytosol, but not processed with charcoal, are included to quantitate amount of available isotope. Also, wells containing radioactivity but no cytosol are processed with charcoal to estimate unremovable DPM of [3H]17β-estradiol. Corning #25880-96 96-well plates were used because, among those tested, they have demonstrated to bind the least amount of estradiol.

Analysis of Results:

Counts per minute (CPM) of radioactivity are automatically converted to disintegrations per minute (DPM) by the Beckman LS7500 Scintillation Counter using a set of quenched standards to generate a H# for each sample. To calculate the % of estradiol binding in the presence of 100 or 500 fold competitor the following formula is applied:

((DPM sample-DPM not removed by charcoal/(DPM estradiol-DPM not removed by charcoal))×100%=% of estradiol binding For the generation of IC$_{50}$ curves, % binding is plotted vs [compound]. IC$_{50}$'s are generated for compounds that show >10% competition at up to a 500×competitor concentration.

Reference Compounds:

Reference compounds and those of Example Nos. 4, 6, 9 and 11 have been evaluated and their IC$_{50}$ concentration determined. The concentration of these compounds required to displace 50% of [3H]17β-estradiol is:

| | |
|---|---|
| estradiol: 0.08 μM | Example No. 4: 0.8 μM |
| tamoxifen: 4.50 μM | Example No. 6: 1.0 μM |
| raloxifene 0.04 μM | Example No. 9: 0.31 μM |
| 17α-dihydroequilin 0.15 μM | Example No. 11: 0.35 μM |

What is claimed is:

1. A compound of the formula:

wherein:

R$_1$ is H or benzyl;

R$_2$ is H, —OH, or —O—benzyl;

R$_3$, R$_4$, and R$_5$ are independently selected from H, cyano, C$_1$–C$_6$ alkyl (straight chain or branched), trifluoromethyl, —OH or the C$_1$–C$_{12}$ esters (straight chain or branched) or C$_1$–C$_{12}$ alkyl ethers (straight chain or branched or cyclic) thereof, halogen, or C$_1$–C$_6$ halogenated ethers;

R$_6$ is H or C$_1$–C$_6$ alkyl;

R$_7$ is C$_1$–C$_6$ alkyl;

n is 2 to 3;

Y is O or S; and

X is

R' is selected from $C_1$–$C_6$ lower alkyl or the moieties:

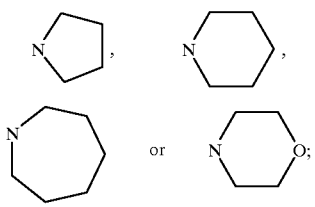

or a pharmaceutically acceptable salt thereof.

2. A compound of claim 1 wherein Y is O and $R_1$, $R_2$, $R_3$, $R_4$, $R_5$, n, X and R' are as defined in claim 1; or a pharmaceutically acceptable salt thereof.

3. A compound of claim 2 wherein n is 2; $R_3$, $R_4$, and $R_5$ are independently selected from H, OH or halogen or a pharmaceutically acceptable salt thereof.

4. A compound of claim 1 which is 5-Benzyloxy-3,3-dimethyl-2-phenyl-1-[4-(2-piperidin-1-yl-ethoxy)-benzyl]-2,3-dihydro-1H-indole or a pharmaceutically acceptable salt thereof.

5. A compound of claim 1 which is 3,3-dimethyl-2-phenyl-1-[4-(2-piperidin-1-yl-ethoxy)-benzyl]-2,3-dihydro-1H-indol-5-ol or a pharmaceutically acceptable salt thereof.

6. A compound of claim 1 which is 1-[4-(2-Azepan-1-yl-ethoxy)-benzyl]-5-benzyloxy-3,3-dimethyl-2-phenyl-2,3-dihydro-1H-indole or a pharmaceutically acceptable salt thereof.

7. A compound of claim 1 which is 1-[4-(2-Azepan-1-yl-ethoxy)-benzyl]-3,3-dimethyl-2-phenyl-2,3-dihydro-1H-indol-5-ol or a pharmaceutically acceptable salt thereof.

8. A compound of claim 1 which is 5-Benzyloxy-2-(4-benzyloxy-phenyl)-3,3-dimethyl-1-[4-(2-piperidin-1-yl-ethoxy)-benzyl]2,3-dihydro-1H-indole or a pharmaceutically acceptable salt thereof.

9. A compound of claim 1 which is 2-(4-Hydroxy-phenyl)-3,3-dimethyl-1-[4-(2-piperidin-1-yl-ethoxy)-benzyl]-2,3-dihydro-1H-indol-5-ol or a pharmaceutically acceptable salt thereof.

10. A compound of claim 1 which is 5-Benzyloxy-2-(4-benzyloxy-phenyl)-3,3-dimethyl-1-[4-(2-Azepan-1-yl-ethoxy)-benzyl]-2,3-dihydro-1H-indole or a pharmaceutically acceptable salt thereof.

11. A compound of claim 1 which is 1-[4-(2-Azepan-1-yl-ethoxy)-benzyl]-2-(4-hydroxy-phenyl)-3,3-dimethyl-2,3-dihydro-1H-indol-5-ol or a pharmaceutically acceptable salt thereof.

12. A pharmaceutical composition comprising a compound of claim 1, or a pharmaceutically acceptable salt thereof, and a pharmaceutically acceptable carrier or excipient.

13. A method of treating bone loss in a mammal, the method comprising administering to a mammal in need thereof an effective amount of a compound of claim 1, or a pharmaceutically acceptable salt thereof.

14. A method of treating disease states or syndromes which are caused or associated with an estrogen deficiency in a mammal, the method comprising administering to a mammal in need thereof an effective amount of a compound of claim 1, or a pharmaceutically acceptable salt thereof.

15. A method of treating cardiovascular disease in a mammal, the method comprising administering to a mammal in need thereof an effective amount of a compound of claim 1, or a pharmaceutically acceptable salt thereof.

* * * * *